US00PP14007P39

(12) United States Plant Patent
Bessho

(10) Patent No.: US PP14,007 P3
(45) Date of Patent: Jul. 22, 2003

(54) PETUNIA PLANT NAMED 'KAKEGAWA S57'

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/989,655

(22) Filed: Nov. 21, 2001

(65) Prior Publication Data

US 2003/0097700 P1 May 22, 2003

(51) Int. Cl.[7] ..... A01H 5/00
(52) U.S. Cl. ..... Plt./356
(58) Field of Search ..... Plt./356

(56) References Cited

U.S. PATENT DOCUMENTS

PP10,310 P * 3/1998 Sakazaki ..... Plt./356

OTHER PUBLICATIONS

UPOV–ROM GTITM Computer Database, 2002/03, GTI Jouve Retrieval Software, citation for 'Kakegawa S57'.*

* cited by examiner

*Primary Examiner*—Bruce R. Campell
*Assistant Examiner*—Susan B. McCormick
(74) *Attorney, Agent, or Firm*—Jondle & Associates PC

(57) ABSTRACT

A Petunia plant particularly distinguished by its lavender flower color and creeping, mounding habit.

1 Drawing Sheet

Genus and species: Petunia hybrida.
Variety denomination: 'Kakegawa S57'.

BACKGROUND OF THE NEW PLANT

The present invention comprises a new and distinct cultivar of Petunia, botanically known as Petunia hybrida, and hereinafter referred to by the cultivar name 'Kakegawa S57'. 'Kakegawa S57' originated from a hybridization made in 1997 in Kakegawa, Japan. The male parent was a phenotypically fixed $F_3$ selection from a cross made in 1994 between two breeding lines, 4UK-1 (not patented) and P-1a (not patented). The female parent of 'Kakegawa S57' was an $F_5$ selection known as 89S-829-1a-1a-1a-1 from a dwarf multiflora pink breeding gene pool. $F_1$ seed from this cross was sown during the summer of 1997.

Two hundred $F_1$ plants were transplanted to the field in Salinas, Calif. during the summer of 1998. Three lines were selected for further evaluation and vegetatively propagated. The three lines were propagated again in 1999 and evaluated for fixed characteristics and ease of propagation. Final selection of one line was made in Salinas, Calif. during the summer of 1999. The line was established as 'Kakegawa S57', and determined to have its characteristics firmly fixed.

'Kakegawa S57' has been found to retain its distinctive characteristics after two years and four cycles of vegetative propagation and this novelty is firmly fixed. The variety has demonstrated stability during this time and has no inherent variation or off-types.

DESCRIPTION OF PHOTOGRAPH

This new Petunia plant is illustrated by the accompanying photograph which shows blooms, and foliage of the plant in full color, the colors shown being as true as can be reasonably obtained by conventional photographic procedures.

DESCRIPTION OF THE NEW CULTIVAR

Figure 1:
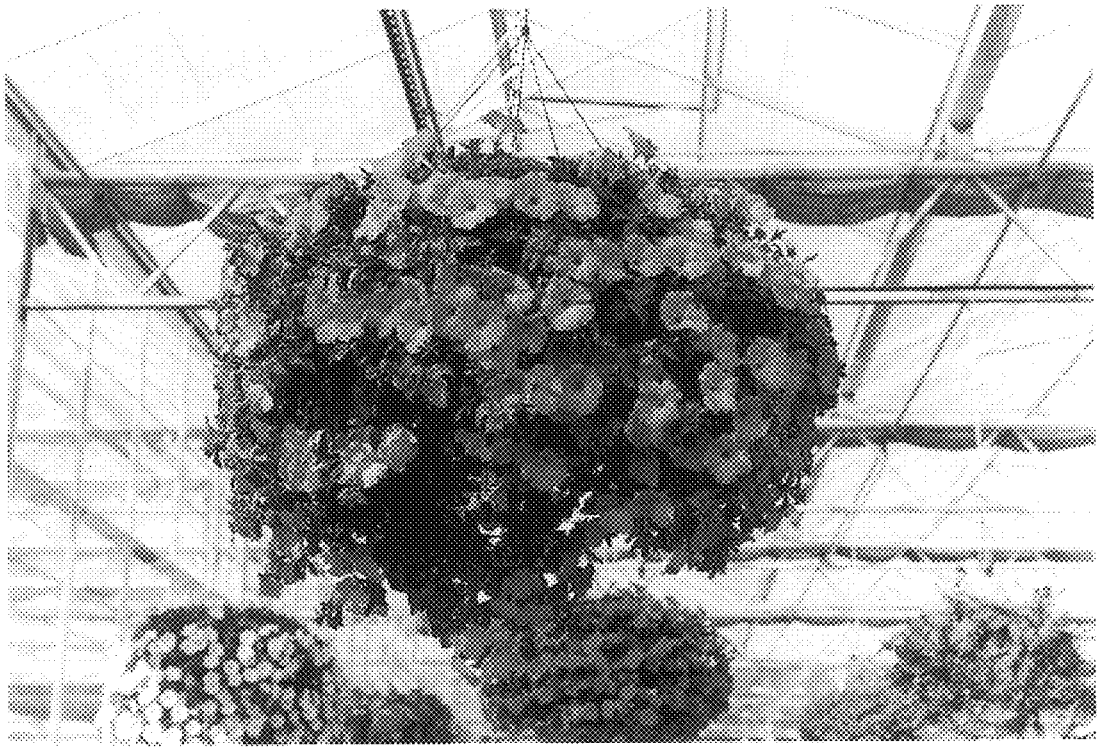
FIG. 1 shows the entire plant approximately eight weeks after transplating a rooted cutting.
Figure 2:
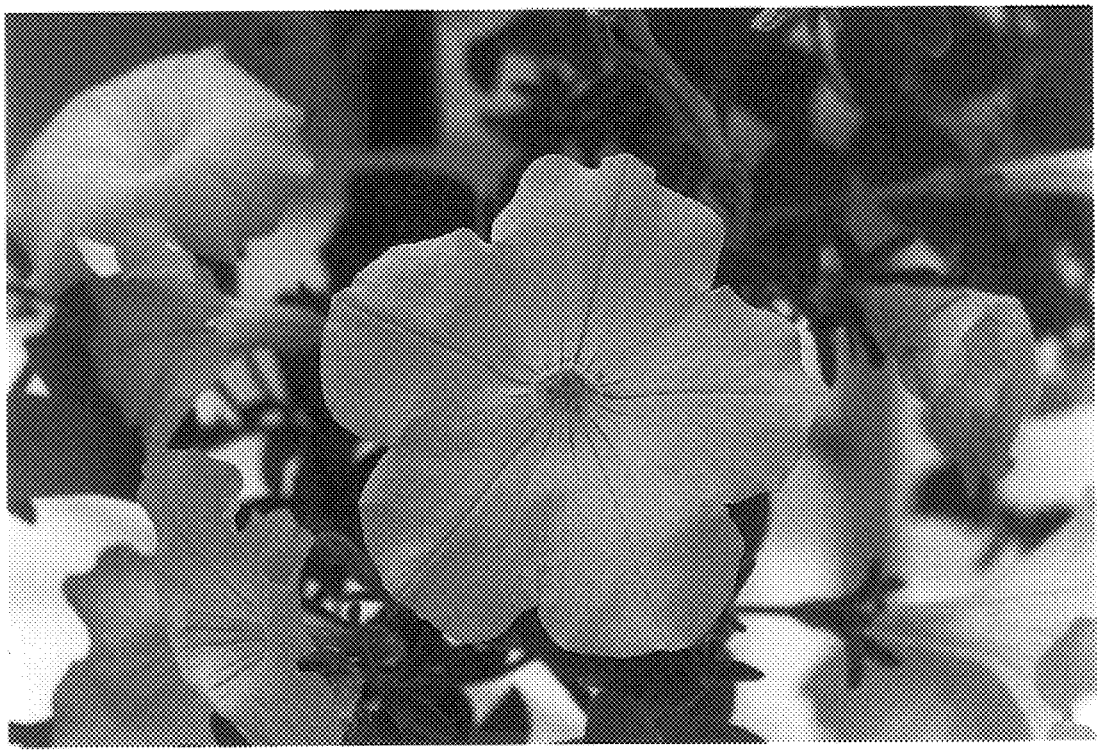
FIG. 2 shows the mature inflorescence.

The following detailed descriptions set forth the distinctive characteristics of 'Kakegawa S57'. The data which defines these characteristics were collected from asexual reproductions carried out in Salinas, Calif. Three plants from fully rooted 15 cm diameter pots were transplanted to one 50 cm diameter hanging baskets and grown in the same conditions. Data was collected on plants in 50 cm diameter pots eight weeks after rooted cuttings were transplanted. Color references are primarily to The R.H.S. Colour Chart of The Royal Horticultural Society of London (R.H.S.).

DESCRIPTION OF THE NEW PLANT

Classification:
- *Botanical.*—Petunia hybrida.
- *Commercial.*—Petunia.

Parentage:
- *Female parent.*—Breeding line 89S-8298-1a-1a-1a-1 (not patented).
- *Male parent.*—An $F_3$ selection from the cross of two breeding lines, 4UK-1 (not patented) and P-1a (not patented).

Environmental conditions for plant growth: Plants were propagated from vegetative cuttings, and grown individually in 15 cm diameter plastic pots in a glass greenhouse located in Salinas, Calif. Pots contained a peat moss-based growing medium. Soluble fertilizer containing 18% nitrogen, 8% phosphorus and 18% potassium was applied in four, daily irrigations. The fifth irrigation was made with non-fertilized water. Pots were top-dressed with a slow release fertilizer containing 18% nitrogen, 8% phosphorus and 18% potassium. The typical average air temperature was 24C.

Growth:
- *Habit.*—Branching.
- *Form.*—Descending.
- *Plant size.*—45 cm total diameter and 25 cm total height.

*Flowering habit.*—Indeterminate.
*Time to initiate root development.*—7 days after sticking cuttings.
*Time to bloom from propagation.*—4–6 weeks after rooting when grown in 10–15 cm diameter plastic pots.
*Life cycle.*—Annual.

Stems:
*Color.*—Yellow-green (RHS 145A).
*Description.*—Round.
*Diameter.*—4–5 mm.
*Internode length.*—4.5 cm.

Leaves:
*Arrangement.*—Opposite.
*Apex.*—Mucronate.
*Base.*—Oblique.
*Color.*—Upper surface is green (RHS 137A) and lower surface is green (RHS 138B).
*Margin.*—Entire.
*Size.*—Length is 8.0–9.0 cm and width is 4.5–5.5 cm.
*Shape.*—Ovate.
*Texture.*—Coarse.
*Venation.*—Pinnate.
*Pubescence.*—Present, clear.

Buds:
*Bud color.*—Yellow-green (RHS 144C).
*Bud diameter.*—5.0 mm.
*Bud length.*—1.8 cm.

Flowers:
*Calyx.*—5 sepals; 2.3 cm×0.5 cm (length×width).
*Corolla.*—5 petals, fused.
*Flower diameter.*—6.0–7.0 cm.
*Fragrant.*—Yes.
*Inflorescence type.*—Solitary.
*Pistil.*—Compound.
*Ovary.*—Superior, parietal placentation.
*Stamens.*—5 total with two long and three short; yellow-green (RHS 150D).
*Style.*—Green (RHS 143C).
*Peduncle.*—2.5–3.0 cm×2 mm (length×width); pubescent.
*Petal color.*—Limbs: upper — purple (RHS 77C); lower — purple (RHS 76A). Tube: Inner — yellow-green (RHS 145B) with purple (RHS 79B) veins; Outside is yellow-green (RHS 149D) with yellow-green (RHS N144A) veins.
*Petal margin.*—Smooth.
*Petal pubescence.*—Absent.
*Tube throat diameter.*—1.0 cm.
*Pollen color.*—Blue (RHS 106D).
*Produces seed.*—Yes; grey-orange (RHS 172B); <1.0 mm diameter; seed coat has netted pattern, 8–10,000 seeds/gram.

Disease and Insect Resistance

No susceptibility to diseases or insects noted to date.

Comparison with Known Cultivars

'Kakegawa S57' is most similar to the variety 'Cascadia Charme' but differs in the following areas: The flowers on 'Kakegawa S57' are smaller than on 'Cascadia Charme' and the corolla tube is less noticeable because there is less difference in limb and tube color. The petal limb color is a more bluish pink than 'Cascadia Charme'. The flowers on the present invention are fragrant while the flowers of 'Cascadia Charme' produce no noticeable fragrance.

Comparison with Parental Cultivars

Table 1 below lists some traits from the parental cultivars as compared to the present invention.

TABLE 1

| Characteristic | 'Kakegawa S57' | 89S-829-1a-1a-1a-1 (female) | 4UK-1 x P-1A (male) |
|---|---|---|---|
| Plant Habit | Creeping/ branching | Dwarf and compact | Creeping |
| Flower Size | Grandiflora | Medium size | Grandiflora |
| Flower Petal Color | Deep Pink | Pink | Pale Pink |

I claim:

1. A new and distinct Petunia plant as shown and described herein.

* * * * *